United States Patent
Takeuchi et al.

(10) Patent No.: US 7,231,332 B2
(45) Date of Patent: Jun. 12, 2007

(54) APPARATUS AND METHOD FOR SIMULATING PHENOMENA OF A PARTICLE FORMED OF SUBSTRATE PARTICLES AND ADSORBATE PARTICLES

(75) Inventors: Munetaka Takeuchi, Chiba (JP); Nozomu Kamiya, Chiba (JP); Hiromi Hayashi, Aomori (JP); Makoto Ishitobashi, Aomori (JP)

(73) Assignee: Fujitsu Limited, Kawasaki (JP)

( * ) Notice: Subject to any disclaimer, the term of this patent is extended or adjusted under 35 U.S.C. 154(b) by 836 days.

(21) Appl. No.: 08/889,440

(22) Filed: Jul. 8, 1997

(65) Prior Publication Data

US 2001/0011208 A1 Aug. 2, 2001

(30) Foreign Application Priority Data

Dec. 19, 1996 (JP) .................................. 8-339624

(51) Int. Cl.
*G06G 7/48* (2006.01)
*G06G 7/58* (2006.01)
(52) U.S. Cl. ............................................. 703/6; 703/12
(58) Field of Classification Search ................ 364/578; 395/500.26; 703/5–6
See application file for complete search history.

(56) References Cited

U.S. PATENT DOCUMENTS

| | | | | |
|---|---|---|---|---|
| 4,370,176 A | * | 1/1983 | Bruel | ........................ 438/514 |
| 5,421,934 A | * | 6/1995 | Misaka et al. | ................. 216/59 |
| 5,602,418 A | * | 2/1997 | Imai et al. | ................... 257/627 |
| 5,714,006 A | * | 2/1998 | Kizuki et al. | ................. 117/89 |
| 5,751,607 A | * | 5/1998 | Ohta | .......................... 364/578 |

OTHER PUBLICATIONS

F. H. Baumann et al., "3D Modeling of Sputter and Reflow Processes for Interconnect Metals," IEDM 95, p. 4.4.1-4.4.4, 1995.*
T. Takagi, "Development of New Materials by Ionized-Cluster Beam Technique," Mat. Res. Soc. Symp. Proc. vol. 27, p. 501-511, 1987.*
H. M. Jones et al., "Monte Carlo Investigation of Electron-Imapct Ionization in Liquid Xenon," Phys. Rev. B, vol. 48, p. 9382-9387, 1993.*
Printout from internet: Cornell Theory Center; A Dynamic Brittle-Ductile Transition in a Simulation of 100 Million Atoms; 10 hand numbered pages, 1996.*
Printout from internet: XSIMBAD Version 2.0; hand numbered pp. 1-12, 1996.*
Kinema/SDK—Programmer's Reference Manual: ArSciMed; chapters 1-10, 1996.*
Bouvier et al.; "From crowd simulation to airbag deployment: particle systems, a new paradigm of simulation"; J. of Electronic Imaging; pp. 94-107, Jan. 1997.*
Yamada et al.; "A sputter equipment simulation system including molecular dynamical target atom scattering model"; IEEE-IEDM 95; pp. 4.5.1 to 4.5.4, 1995.*

(Continued)

*Primary Examiner*—Hugh Jones
(74) *Attorney, Agent, or Firm*—Staas & Halsey LLP

(57) ABSTRACT

An apparatus and method for simulating phenomena of a combined particle formed of substrate particles and adsorbate particles. The simulated phenomena can include, for example, crystal growth, crystal surface adsorption and surface damage. The apparatus includes a kinetic condition setting unit and a particle motion computing unit. The kinetic condition setting unit sets information for defining kinetic conditions of the adsorbate particles. The particle motion computing unit generates the adsorbate particles in accordance with the information set by the kinetic condition setting unit and computes motion of the generated adsorbate particles, to simulate phenomena of the combined particle.

28 Claims, 13 Drawing Sheets

OTHER PUBLICATIONS

Cohen; "Computer animations, quantum mechanics and elementary particles"; Europhys. News; pp. 163-166, 1992.*
Reeves; "Particle systems-a technique for modeling a class of fuzzy objects"; ACM Trans. Graphics; pp. 359-376, 1983.*
Husinsky et al.; "Fundamental aspects of SNMS for thin film characterization: experimental studies and computer simulations"; Thin Solid Films; pp. 289-309, Jan. 1996.*
Printout of "ewals3.F90" from Appellants' CD ROM (p. 2, paper # 36); pp. 1-8.*
Printout of "TABLEM_Cell" from Appellansts' CD ROM (p. 2, paper # 36); pp. 1-6.*
Screenshots of CD ROM directory and attempts to open "F90" files (Appellants's CD ROM; p. 2, paper # 36); pp. 1-3.*
Appellants' Assignee's website—Google search; one page.*
Printout from Assignee's webpage (Cache Group)—two pages.*
Printout from Assignees's website—"Materials Explorer"—see p. 4, par. 3, paper # 34; two pages.*
"Materials Explorer" (Parts 1-3); pp. 1-196; pp. 1-38; pp. 1-37, respectively; 2001; Printed from Appellants' website.*
"*Molecular-dynamics simulations for molecular-beam epitaxy: Overlayer growth pattern in two-component Lennard-Jones systems*", published in The American Physical Society, pp. 9476-9485 (1989).
"*Molecular-Dynamics Simulations of Hydrogenated Amorphous Silicon Thin-Film Growth*", presented at the Fall Meeting of the Materials Research Society, Boston, MA, Nov. 27-Dec. 1, 1995.

* cited by examiner

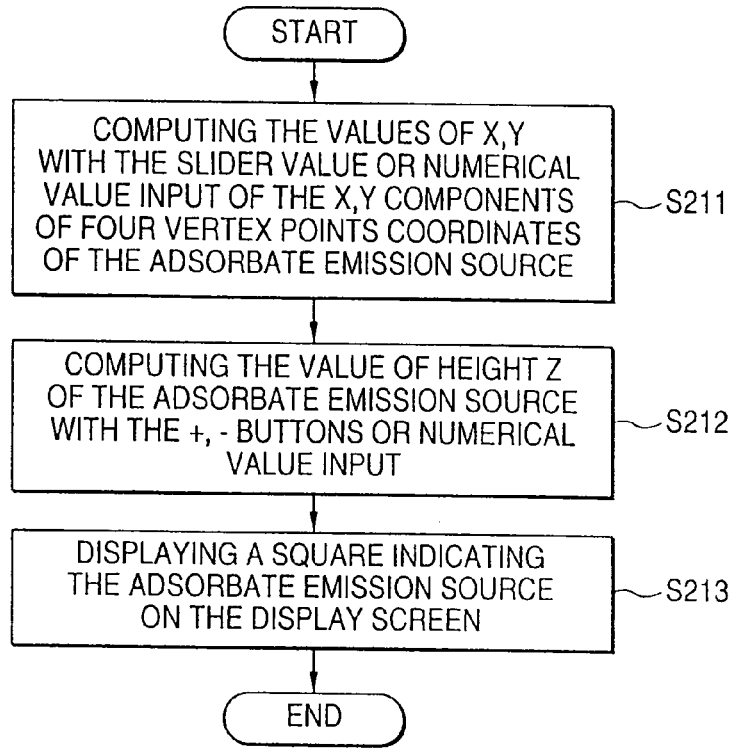
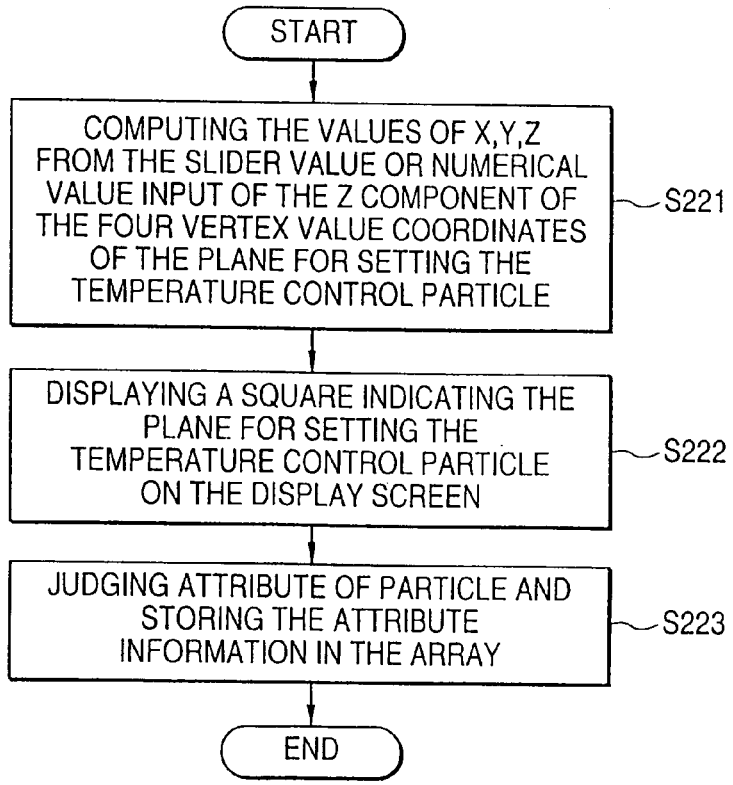

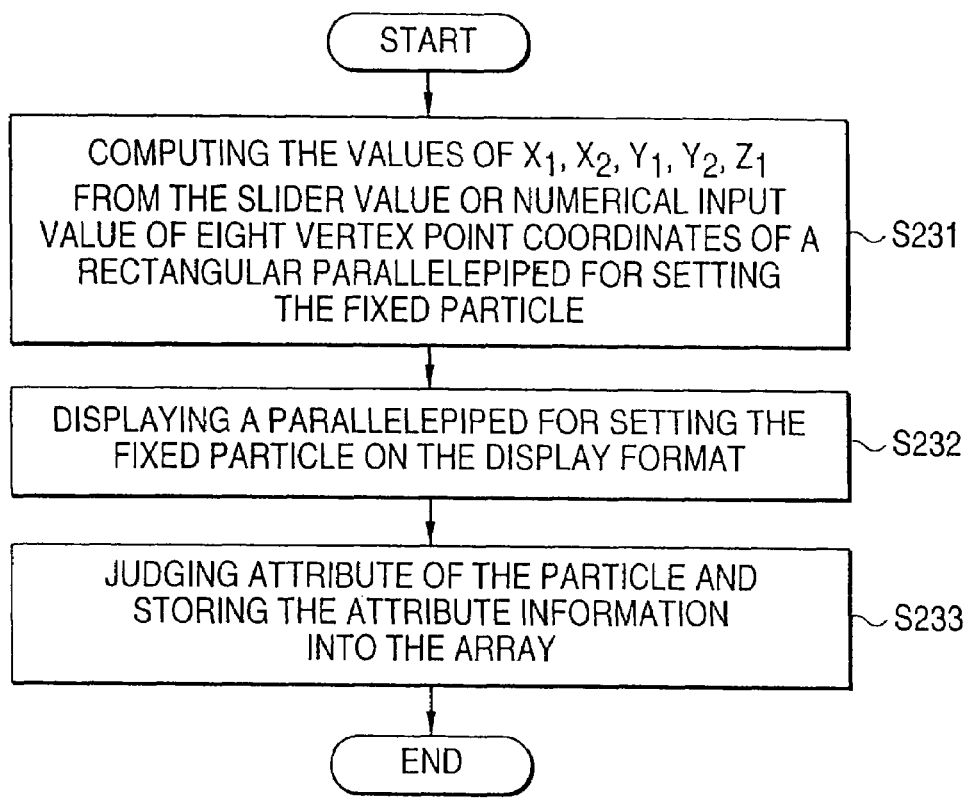
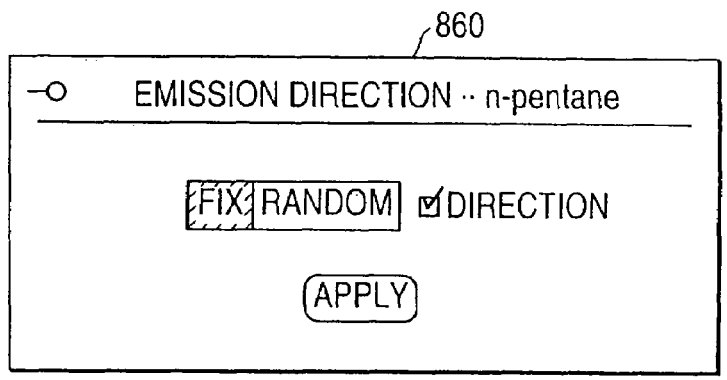

FIG. 8

GENERATION SCHEDULE

800 — 
| NO. | COMPONENT | TOTAL GENERATIVE NUMBER |
|---|---|---|
| ◆ 1 | n - pentane | 5 |
| ◇ 2 | triphenylmethane | 5 |
| ◇ 3 | | |
| ◇ 4 | | |

810 — SIMULATING STEP [STEP] : 10001
820 — SIMULATING TIME [ps] : 10.001000
830 — GENERATION INTERVAL : ◆ EQUAL  ◇ RANDOM

[DELETE]       840        850

| NO. | INTERVAL[STEP] | NUMBER | AVERAGE[STEP] |
|---|---|---|---|
| ◇ 1 | 5000 | 5 | 1000 |
| ◇ 2 | 5001 | 0 | NONE |
| ◇ 3 | | | |
| ◇ 4 | | | |

[OK]   [APPLY]   [CANCEL]

| ADSORBATE PARTICLE INDENTIFIER | STEP NO. |
|---|---|
| 3 | 1222 |
| 3 | 1606 |

FIG. 9

PHYSICAL CONDITION

SOURCE

| NO. | COMPONENT | INITIAL TEMPERATURE [K] |
|-----|-----------|-------------------------|
| ◆ 1 | n - pentane | 300.0000 |
| ◇ 2 | triphenylmethane | 500.0000 |
| ◇ 3 | | |
| ◇ 4 | | |

— 760

INITIAL TEMPERATURE [K]  300.0000    — 770
COMPONENT            ◆ EQUAL  ◆ MAXWEL    — 780
INTERNAL DEGREE OF   ◆ ALL  ◆ NONE
FREEDOM              ■ ORIENTATION
                     ■ DIRECTION    — 790

[OK]            [APPLY]            [CANCEL]

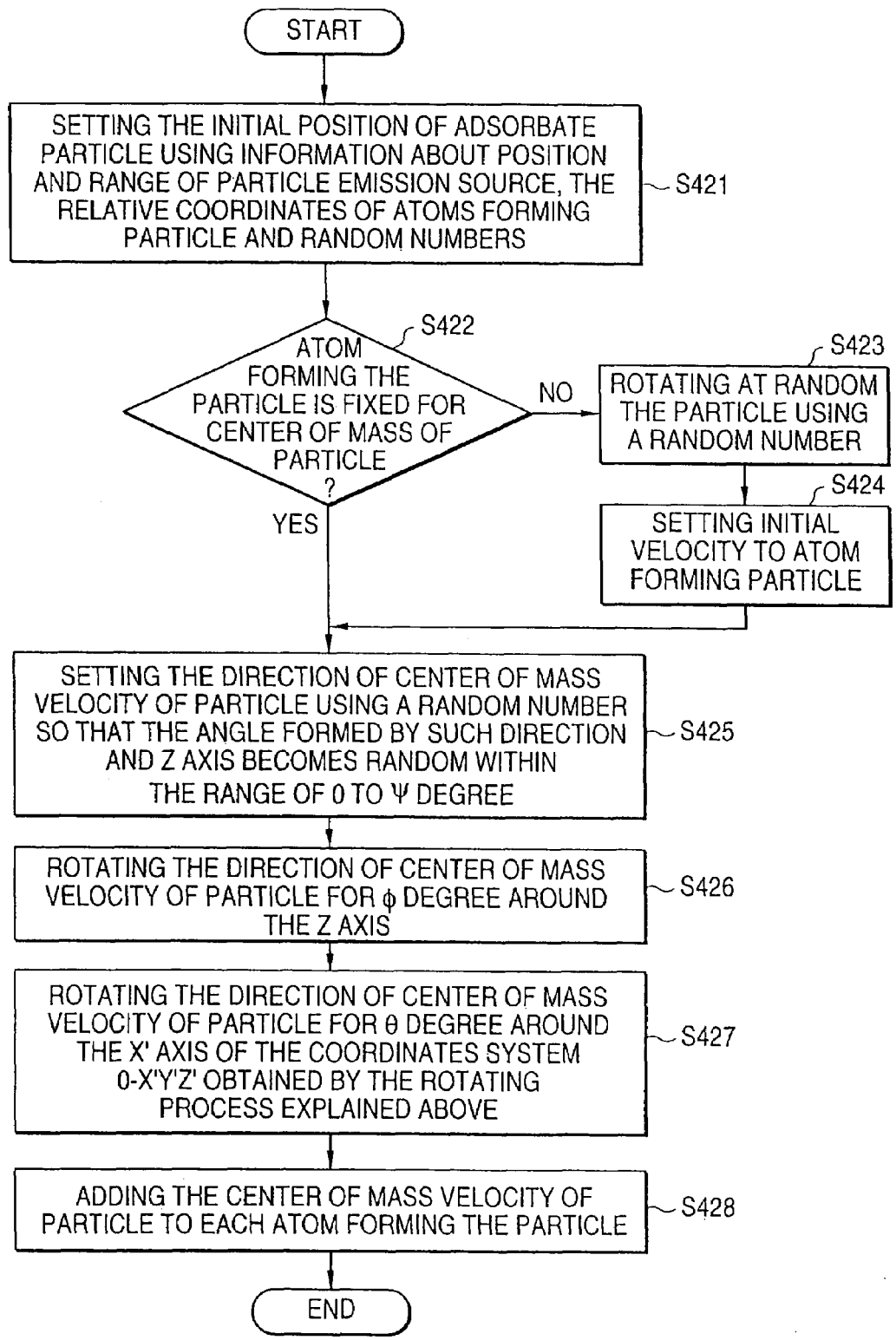

FIG. 15

| | | | |
|---|---|---|---|
| 71 | 3 | | NUMBER OF ADSORBATE PARTICLES |
| 72 | 1 | 2 | 3 | IDENTIFIER OF ADSORBATE PARTICLE |
| 73 | 100.0 | 200.0 | 300.0 | INITIAL TEMPERATURE OF ADSORBATE PARTICLE |
| 74 | 0 | 1 | 0 | (0) EACH ATOM IS NOT FIXED<br>(1) EACH ATOM IS FIXED: FOR CENTER OF MASS OF PARTICLE |
| 75 | 10 | 20 | 30 | NUMBER OF ATOMS FORMING THE ADSORBATE PARTICLE |
| 76 | 1.0,..., 5.0 1.0,..., 5.0 1.5,..., 5.5<br>1.5,..., 5.5 0.5,..., 2.5 1.0,..., 5.0<br>0.5,..., 2.5 1.5,..., 5.5 0.5,..., 2.5 | | | X COORDINATE VALUE<br>Y COORDINATE VALUE<br>Z COORDINATE VALUE OF ATOMS FORMING THE ADSORBATE PARTICLE |
| 77 | 1 | 0 | 1 | GENERATION INTERVAL OF ADSORBATE PARTICLE<br>0 : EQUAL INTERVAL;<br>1 : UNEQUAL INTERVAL; |
| 78 | 1 | 2 | 3 | NUMBER OF PERIODS FOR GENERATION OF ADSORBATE PARTICLE |
| 79 | 1 | 1,1000 | 1,1000,2000 | STARTING STEP OF EACH GENERATION PERIOD OF EACH ADSORBATE PARTICLE |
| 80 | 0 | 0,3 | 1,2,0 | NUMBER OF PARTICLES GENERATED IN EACH GENERATION PERIOD OF EACH ADSORBATE PARTICLE |
| 81 | 180.0 | 150.0 | 120.0 | PARTICLE EJECTING IN DIRECTION $\theta$ |
| 82 | 0.0 | 120.0 | 240.0 | PARTICLE EJECTING IN DIRECTION $\phi$ |
| 83 | 0.0 | 30.0 | 10.0 | DISTRIBUTION ANGLE $\psi$ OF PARTICLE EJECTING DIRECTION |
| 84 | 5.0 | 0.0 | 20.0 | POSITION OF PARTICLE EMISSION SOURCE (X,Y,Z COORDINATE VALUES) |
| 85 | 10.0 | 20.0 | | SIZE OF PARTICLE EMISSION SOURCE (LENGTH IN X,Y DIRECTIONS) |
| 86 | 500 | | | NUMBER OF SUBSTRATE ATOMS |
| 87 | 1.0, 2.0,...,20.0<br>1.0, 2.0,...,20.0<br>1.0, 2.0,...,6.0 | | | X COORDINATE VALUE OF ATOMS FORMING A SUBSTRATE<br>Y COORDINATE VALUE OF ATOMS FORMING A SUBSTRATE<br>Z COORDINATE VALUE OF ATOMS FORMING A SUBSTRATE |
| 88 | 0, 1, 2,..., 2, 1, 0 | | | ATTRIBUTE OF ATOMS FORMING A SUBSTRATE<br>0: FREE MOTION<br>1: TEMPERATURE CONTROL<br>2: STATIONARY |

APPARATUS AND METHOD FOR SIMULATING PHENOMENA OF A PARTICLE FORMED OF SUBSTRATE PARTICLES AND ADSORBATE PARTICLES

CROSS-REFERENCE TO RELATED APPLICATIONS

This application is based on, and claims priority to, Japanese patent application 08-339624, filed Dec. 19, 1996, in Japan, and which is incorporated herein by reference.

BACKGROUND OF THE INVENTION

1. Field of the Invention

The present invention relates to an apparatus and method for simulating phenomena, such as crystal growth, surface adsorption and surface damage, of a particle formed of substrate particles and adsorbate particles.

2. Description of the Related Art

Experimental processes have been proposed to detect and analyze the molecular details (such as, for example, film forming processes, process conditions and surface structure) of new materials. These proposed experimental processes include, for example, the use of a scanning tunneling microscope (STM) or an atomic force microscope (AFM). Unfortunately, such experimental processes are often inadequate at providing the required level of detection and analysis.

Therefore, it is often required to simulate a phenomena at the atomic and/or molecule level to detect various processes involved in the phenomena. The simulated phenomena can include, for example, crystal growth, surface adsorption and surface damage of a material or structure.

Simulation has been attempted by a molecular dynamics method, but it has been very difficult to manually execute such simulation. For example, the simulation requires different data of various particles to be input to the simulation process for molecular dynamics computation. Thus, the required data includes a large amount of different data for each simulation particle. This different data must be manually entered. The simulation particles include, for example, atoms and molecules.

Therefore, a program has been developed to generate molecule data for each particle. However, the generation of the molecule data requires a relatively long time since the program must be run separately for each individual particle to generate data for the particle. Moreover, different programs must be run to generate data for different phenomena.

SUMMARY OF THE INVENTION

Accordingly, it is an object of the present invention to provide a more flexible simulation system to simulate various phenomena such as crystal growth, surface adsorption, and surface damage.

It is an additional object of the present invention to provide a simulation system that generates and analyzes a plurality of atoms, molecules and particles to simulate many different phenomena.

It is a further object of the present invention to provide a simulation system which considers motion of a particle (that is, the timing for the motion of the particle) and the initial position of the particle (that is, the starting point of motion).

Additional objects and advantages of the invention will be set forth in part in the description which follows, and, in part, will be obvious from the description, or may be learned by practice of the invention.

The foregoing objects of the present invention are achieved by providing an apparatus for simulating phenomena of a combined particle formed of individual particles. For example, a combined particle refers to a particle formed of a combination of individual atoms and/or molecules. The apparatus includes a kinetic condition setting unit and a particle motion computing unit. The kinetic condition setting unit sets information for defining a plurality of generation periods and a corresponding number of individual particles to be generated during each generation period. The particle motion computing unit generates the individual particles in accordance with the information set by the kinetic condition setting unit and computes motion of the generated individual particles, to simulate phenomena of the combined particle. The combined particle is formed, for example, of substrate particles and adsorbate particles, where each of the individual particles is an adsorbate particle.

Objects of the present invention are also achieved by providing an apparatus for simulating phenomena of a combined particle formed of individual particles, where each individual particle has a corresponding emission source. The apparatus includes an input device, a kinetic condition setting unit and a particle motion computing unit. The input device allows a user to designate a region. The kinetic condition setting unit, for each individual particle, sets the region designated by the user as a region indicating a position of the corresponding emission source. The particle motion computing unit generates the individual particles in accordance with the position of the corresponding emission source as indicated by the region designated by the user and computes motion of the generated individual particles, to simulate phenomena of the combined particle.

Moreover, objects of the present invention are achieved by providing an apparatus for simulating phenomena of a combined particle formed of individual particles. The apparatus includes a kinetic condition setting unit and a particle motion computing unit. The kinetic condition setting unit sets information for defining kinetic conditions of the individual particles. The particle motion computing unit generates the individual particles in accordance with the information set by the kinetic condition setting unit and computes motion of the generated individual particles, to simulate phenomena of the combined particle.

In addition, objects of the present invention are achieved by providing an apparatus for simulating phenomena of a combined particle formed of substrate particles and adsorbate particles. The apparatus includes a kinetic condition setting unit and a particle motion computing unit. The kinetic condition setting unit sets information for defining kinetic conditions of the adsorbate particles. The particle motion computing unit generates the adsorbate particles in accordance with the information set by the kinetic condition setting unit and computes motion of the generated adsorbate particles, to simulate phenomena of the combined particle.

Objects of the present invention are further achieved by providing a method for simulating phenomena of a combined particle formed of individual particles. The method includes the steps of (a) setting information for defining a plurality of generation periods and a corresponding number of individual particles to be generated during each generation period, (b) generating the individual particles in accordance with the information set in the setting step, and (c) computing motion of the generated individual particles, to simulate phenomena of the combined particle.

Moreover, objects of the present invention are achieved by providing a method for simulating phenomena of a combined particle formed of individual particles, each individual particle having a corresponding emission source. The method includes the steps of (a) setting, for each individual particle, a region indicating a position of the corresponding emission source, (b) generating the individual particles in accordance with the position of the corresponding emission source as indicated by the region set in the setting step, and (c) computing motion of the generated individual particles, to simulate phenomena of the combined particle.

BRIEF DESCRIPTION OF THE DRAWINGS

These and other objects and advantages of the invention will become apparent and more readily appreciated from the following description of the preferred embodiments, taken in conjunction with the accompanying drawings of which:

FIG. 5 is a flowchart illustrating a processing sequence for designating a position and a region of an adsorbate particle emission source, according to an embodiment of the present invention.

FIG. 6 is a flowchart illustrating a processing sequence for setting a fixed particle, according to an embodiment of the present invention.

FIG. 7 is a flowchart illustrating a processing sequence for setting a temperature control particle, according to an embodiment of the present invention.

FIG. 8 is a diagram illustrating a display format for setting an adsorbate particle generation schedule, according to an embodiment of the present invention.

FIG. 9 is a diagram illustrating a display format for setting physical conditions of an adsorbate particle, according to an embodiment of the present invention.

FIG. 11 is a diagram illustrating a display format for setting an adsorbate particle ejecting direction, according to an embodiment of the present invention.

FIG. 14 is a flowchart illustrating a processing sequence for generating an adsorbate particle, according to an embodiment of the present invention.

FIG. 15 is a diagram illustrating a kinetic conditions setting file for setting kinetic conditions of different particles, according to an embodiment of the present invention.

FIG. 16 is a diagram illustrating an adsorbate particle generation table, according to an embodiment of the present invention.

DESCRIPTION OF THE PREFERRED EMBODIMENTS

Figure 1:
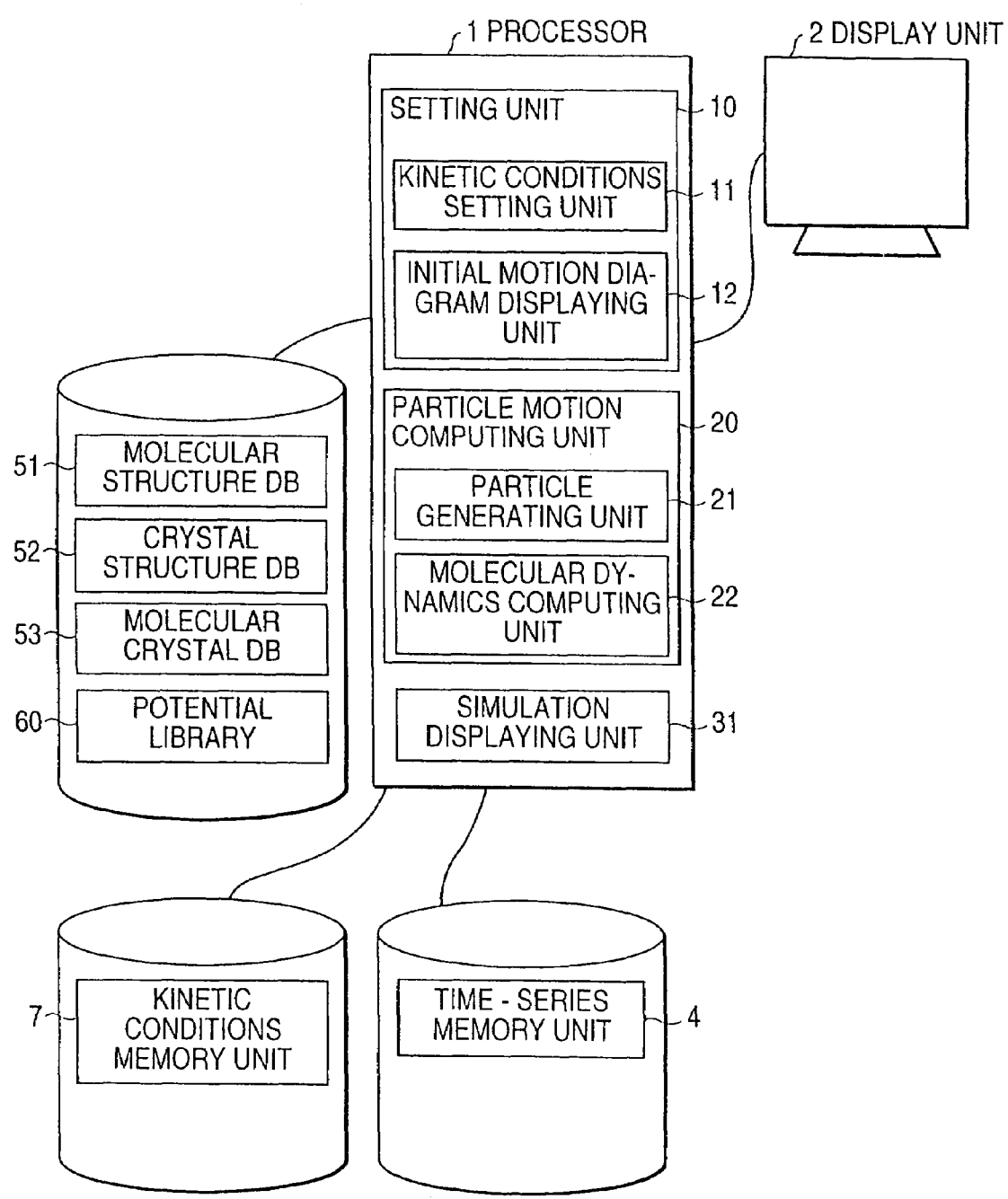
FIG. 1 is a diagram illustrating a particle simulation system, according to an embodiment of the present invention.

Reference will now be made in detail to the present preferred embodiments of the present invention, examples of which are illustrated in the accompanying drawings, wherein like reference numerals refer to like elements throughout.

FIG. 1 is a diagram illustrating a particle simulation system, according to an embodiment of the present invention. Referring now to FIG. 1, a processor 1 is connected to a display unit 2. Processor 1 includes a setting unit 10 and a particle motion computing unit 20. Setting unit 10 includes a kinetic conditions setting unit 11 for setting kinetic conditions of particles to be simulated, and an initial motion diagram displaying unit 12 for providing a graphic display of the contents set by kinetic conditions setting unit 11 on display unit 2. Particle motion computing unit 20 includes a particle generating unit 21 for generating particles depending on the contents preset by kinetic conditions setting unit 11, and a molecular dynamics computing unit 22 for computing "interaction" of particles (atoms or molecules) as a computation object in order to compute motion on a time-series basis. Processor 1 also includes a simulation displaying unit 31 for displaying, on display unit 2, motion of particles obtained by particle motion computing unit 20.

The particle simulation system includes a molecular structure database (DB) 51, a crystal structure database (DB) 52 and a molecular crystal database (DB) 53. These databases store atomic structure information of molecules and crystals. Via kinetic conditions setting unit 11, an operator can select a particle as the object of simulation from molecular structure DB 51, crystal structure DB 52 or molecular crystal DB 53. Molecular dynamics computing unit 22 computes motion of a particle using the atomic structure information corresponding to the selected particle.

A potential library 60 is an aggregation of programs for computing "interaction" (potential) between particles (atoms or molecules). An operator is requested to designate the "interaction" (for example, van der Waals force, Coulomb force, etc.) to be considered between selected particles. Molecular dynamics computing unit 22 then computes motion between particles using the program for obtaining the relevant "interaction" from potential library 60 depending on the designation contents.

A kinetic conditions memory unit 7 stores the kinetic conditions preset by kinetic conditions setting unit 11 and particle motion computing unit 20 computes particle motion depending on the kinetic conditions stored in kinetic conditions memory unit 7. A time series memory unit 4 stores the results computed by particle motion computing unit 20 on the time series basis and simulation displaying unit 31 executes, on the time series basis, a graphic display for the contents of time series memory unit 4 on display unit 2. An operator can observe the simulation result of a particle through the graphic display on display unit 2.

In the following embodiments of the present invention, a particle as a simulation object is composed, for example, of a substrate particle and an adsorbate particle. The substrate particle can be observed, from the external side, as a stationary particle during, for example, film formation. However, with a substrate particle, a relatively small amount of molecule motion may still occur at the molecule level. The adsorbate particle is a particle colliding with a stationary particle during, for example, film formation. Moreover, a substrate particle includes a fixed particle which does not change its position, a temperature control particle of constant temperature, and a free particle having no restriction on change of position and temperature.

Figure 2:
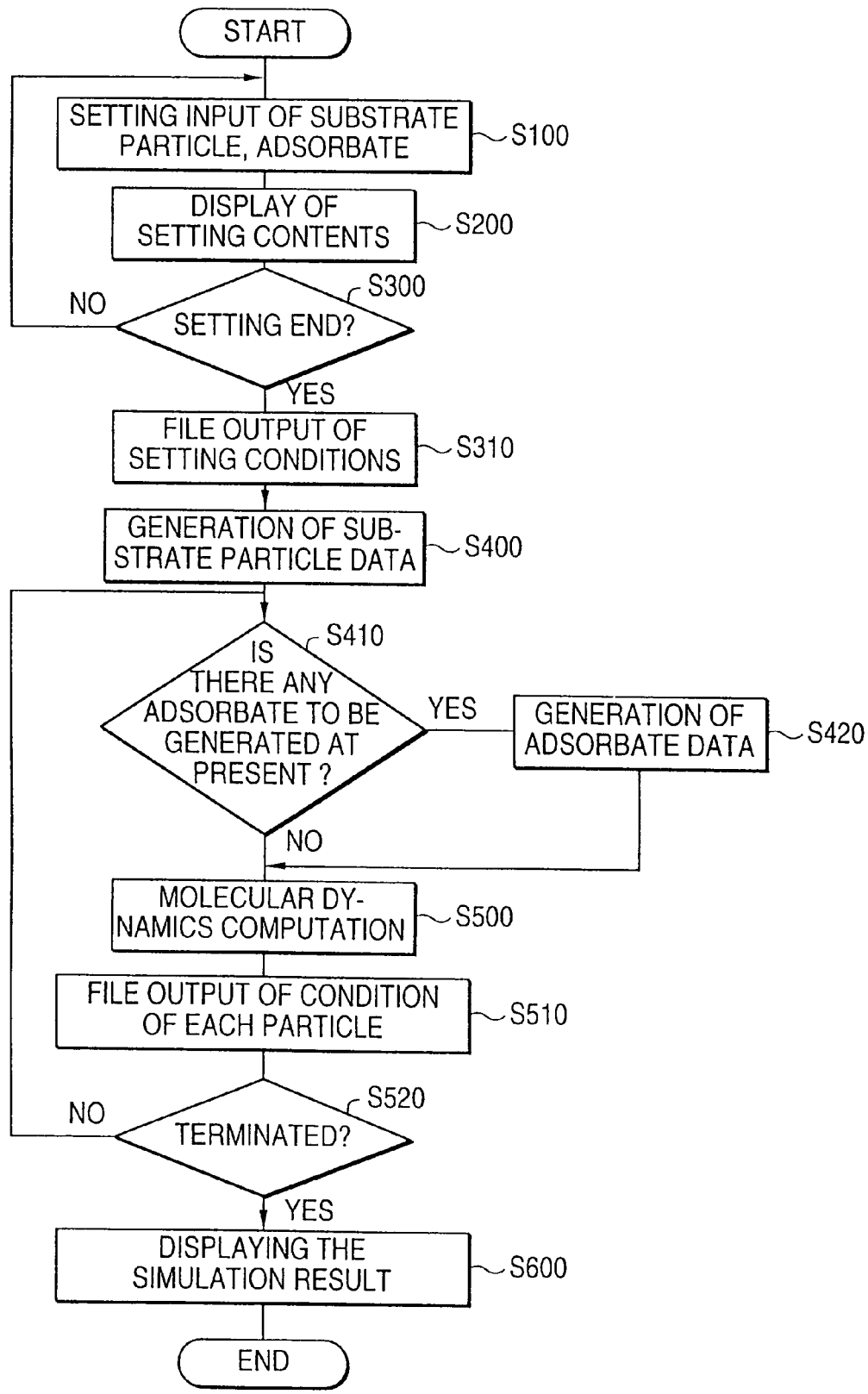
FIG. 2 is a flowchart illustrating a processing sequence of the particle simulation system illustrated in FIG. 1, according to an embodiment of the present invention.

FIG. 2 is a flowchart illustrating a processing sequence of the particle simulation system illustrated in FIG. 1, according to an embodiment of the present invention. More specifically, FIG. 2 illustrates a process for setting kinetic conditions of various particles (such as atoms or molecules) forming a larger particle (such as a molecule), computing motion of the various particles, and producing a computation result.

Referring now to FIG. 2, regarding the setting of a simulation object, in step S100, kinetic conditions setting unit 11 of setting unit 10 causes an operator to input various settings for a particle which is the object of simulation. More specifically, an operator inputs settings for a substrate particle and an adsorbate particle. For example, in step S100, an operator sets the time, position, direction and velocity of an adsorbate particle to be generated, and also sets an attribute of a substrate particle. Moreover, in the step S100, practical substances to be used as the adsorbate particle and substrate particle can be selected by an operator from molecular structure DB 51, crystal structure DB 52 or molecular crystal DB 53.

From step S100, the process moves to step S200, where initial motion diagram display unit 12 of setting unit 10 graphically displays the settings on the display unit. Since the condition of each particle is graphically displayed in step S200, an operator can check the influence of the settings in the simulation object as a whole. From step S200 the process moves to step S300, where it is determined whether the settings are complete. If all the settings are not complete in step S300, the process returns to step S100. If all the settings are complete in step S300, the process moves to step S310, where kinetic conditions memory unit 7 stores the settings set by setting unit 10.

From step S310, the process moves to step S400, where the initial process of simulation is executed to generate the substrate particle data depending on the substrate particle information set in step S100. Unlike the adsorbate particle, the initial number of substrate particles is equal to the number of substrate particles after a certain period of time. Therefore, the substrate particle is generated before the start of simulation. Moreover, regarding the adsorbate particle, data indicating the timing and type of particle is generated. After step S400, a simulation process is sequentially executed for each passage of a unit of time.

More specifically, from step S400 the process moves to step S410, where it is determined whether there is data for an adsorbate particle to be generated at the present time. In step S410, if there is data for an adsorbate particle to be generated, the process moves to step S420 where an appropriate adsorbate particle is generated. From step S420, the process moves to step S500. In step S410, if there is no data for an adsorbate particle to be generated, the process moves to step S500.

In step S500, a molecular dynamics computation is performed for substrate particles and adsorbate particles that have been generated. From step S500, the process moves to step S510, where the result of the molecular dynamics computations is output as a file. From step S510, the process moves to step S520, where it is determined whether a specific period of time has elapsed. If the specific period of time has not elapsed in step S520, the process returns to step S410 to potentially generate additional adsorbate particles and perform additional molecular dynamics computations. When the specific period of time has elapsed in step S520, the process moves to step S600, where the molecular dynamics computation for the simulation is stopped. Moreover, in step S600, depending on the instructions of an operator, the simulation result is graphically displayed. More specifically, the conditions (coordinates, etc.) of each particle are stored, on a time series basis, in the file which is storing the result of the molecular dynamics computation, and such data is graphically displayed.

Figure 3:
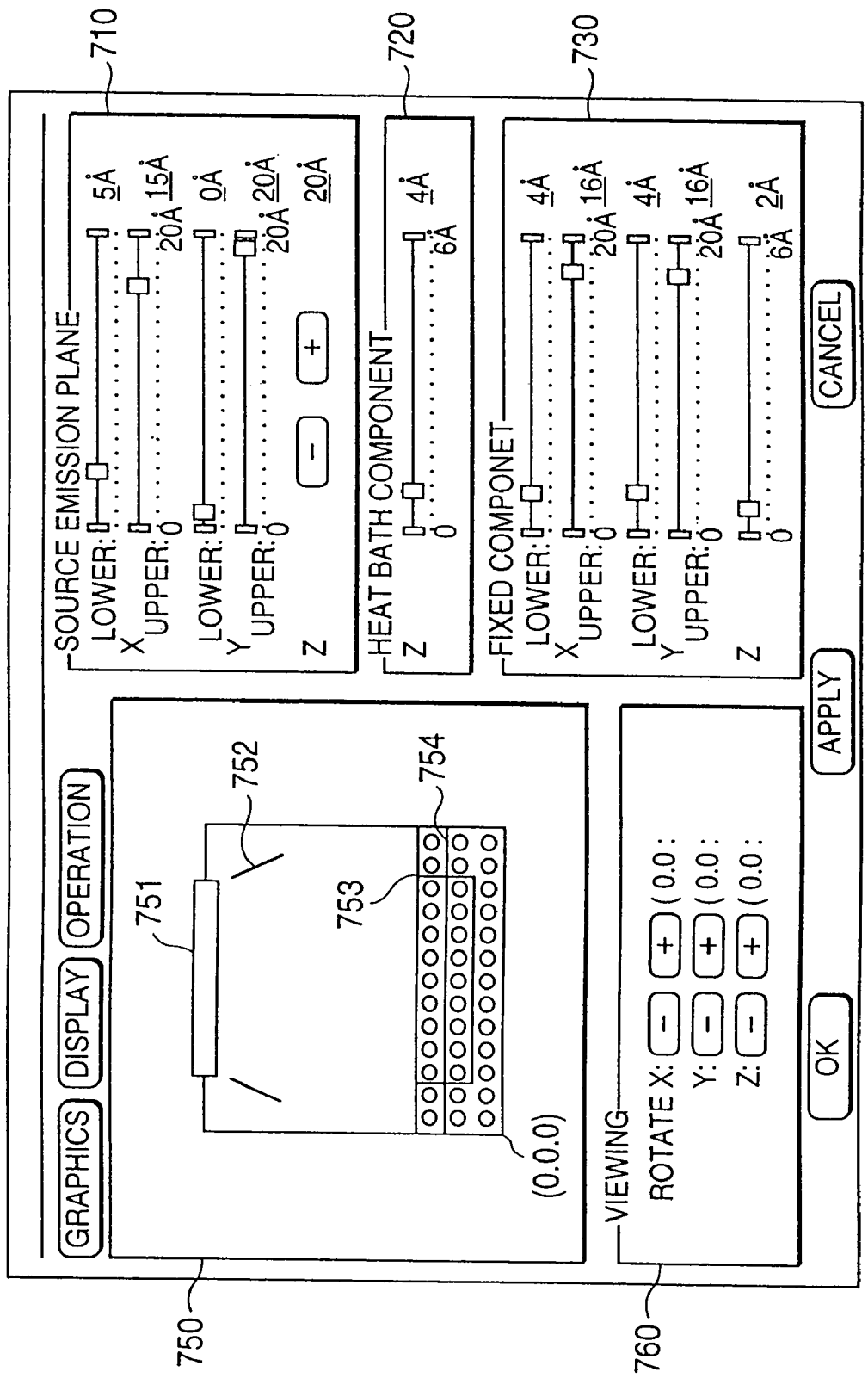
FIG. 3 is a diagram illustrating a display format for setting an adsorbate particle and a substrate particle, according to an embodiment of the present invention.

FIG. 3 which is a diagram illustrating a display format for setting an adsorbate particle and a substrate particle, according to an embodiment of the present invention.

Referring now to FIG. 3, the display screen includes (a) a setting display 710 of an adsorbate particle emission source (Source Emission Plane), (b) a setting display 720 of a temperature control particle (Heat Bath Component) of a substrate particle, (c) a setting display 730 of a fixed particle (Fixed Component) of the substrate particle, (d) a graphic display 750 for displaying the relationship between the adsorbate particle and the set information of the substrate particle and (e) a display (Viewing) 760 for changing the viewing direction of graphic display 750.

Graphic display 750 shows a region 751 of the adsorbate particle emission source, while line 752 shows the adsorbate particle generated with a specific maximum angle and with a specific maximum initial velocity from region 751. Ranges 753 and 754 illustrate ranges of attributes of the substrate particle. More specifically, range 753 is a range of the fixed particle and range 754 is a range of the temperature control particle. These ranges are identical to the contents set by an operator through a setting display and which are displayed by initial motion diagram displaying unit 12 of setting unit 10.

The display screen provides two different methods to input information to setting displays 710, 720 and 730. In one method, an operator can input a value by moving a square mark representing a "slider" to the right or left using a mouse (or a "+" button and a "−" button). In the other method, an operator clicks in the position of the value being displayed with a mouse and then inputs the value by pressing a specific key.

Figure 4:
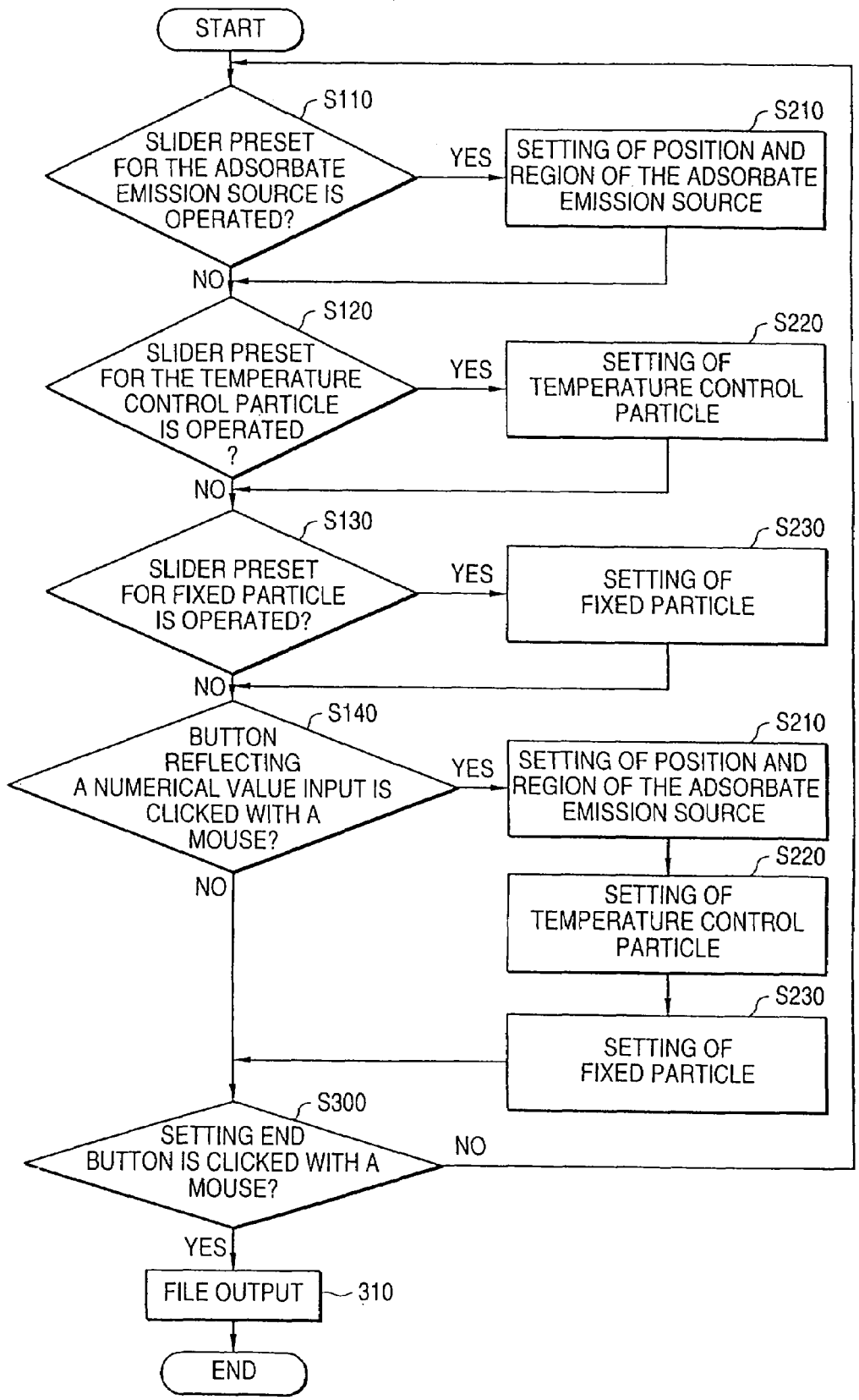
FIG. 4 is a flowchart illustrating a processing sequence for setting an adsorbate particle emission source and substrate particle attribute, according to an embodiment of the present invention.

FIG. 4 is a flowchart illustrating a processing sequence for setting an adsorbate particle emission source and a substrate particle attribute, according to an embodiment of the present invention. Referring now to FIG. 4, in step S110, it is judged whether the slider in display 710 (see FIG. 3) for setting the adsorbate particle emission source is being operated. If the slider is being operated, the process moves to step S210, where a process is executed for setting the position and region of the adsorbate particle emission source.

In step S120, it is judged whether the slider in display 720 (see FIG. 3) for setting the temperature control particle of a substrate particle is being operated. If the slider is being operated, the process moves to step S220, where a process is executed for setting the temperature control particle.

In step S130, it is judged whether the slider in display 730 (see FIG. 3) for setting the fixed particle of a substrate particle is being operated. If the slider is being operated, the process moves to step S230, where a process is executed for setting the fixed particle.

In step S140, it is judged whether, after a numerical value is input by an operator using numerical keys, a button is depressed which indicates the input of the numerical value. (For example, in FIG. 3, this button corresponds to the "Apply" button.) When it is judged that the button is depressed in step S140, the process moves step S210 where the position and region of the adsorbate particle emission source is set in accordance with the numerical value input by the operator. From step S210, the process moves to step S220 where the temperature control particle is set in accordance with the numerical value input by the operator. From step S220, the process moves to step S230 where the fixed particle is set in accordance with the numerical value input by the operator.

In step S300, it is judged whether a setting end button (for example, the "OK" button in FIG. 3) is depressed or not. When the setting end button is not depressed in step S300, the process returns to step S110, so that information will continue to be input. When the setting end button is depressed in step S300, the setting contents are stored in a file in kinetic conditions memory unit 7 (see FIG. 1). This file may hereinafter be referred to as the "kinetic conditions setting file" and is illustrated as kinetic conditions setting file 70 of FIG. 15.

FIG. 5 is a flowchart illustrating a processing sequence for designating a position and a region of an adsorbate particle emission source, according to an embodiment of the present invention. Therefore, FIG. 5 corresponds to the process illustrated in step S210 in FIG. 4.

In FIG. 5, an operator designates the adsorbate particle emission source as a region. Thereby, setting can be done at one time for a plurality of adsorbate particles instead of individually setting the position of the adsorbate particle emission source for each adsorbate particle. For the actual emission source of each adsorbate particle, the specific positioning in the designated region is determined using random numbers, as described in more detail further below.

Moreover, an operator is requested to designate the adsorbate particle generating region as a range on an X coordinate, a region on a Y coordinate and a value on a Z coordinate of an X, Y, Z coordinate system. The origin of the coordinate system is set at the lower left position in graphic display 750 of FIG. 3.

Referring now to FIG. 5, in step S211, when an appropriate slider is operated, the value to be set is computed, depending on the position of the slider. From step S211, the process moves to step S212 where, when the "+" button and "−" button are depressed, the numerical value is increased or decreased, depending on the number of times of depression and depression time. From step S212, the process moves to step S213 where, based on the range of X coordinate, the range of Y coordinate and the value of Z coordinate computed in step S211, the diagram of graphic display 750 (see FIG. 3) is displayed again.

As previously explained, a substrate particle includes a fixed particle which does not change its position, a temperature control particle having a constant temperature and a free particle which is not restricted in change of position and temperature. In this particle simulation system, an operator is requested, regarding the setting of the region for the fixed particle, to set a combined region for both the temperature control particle and the free particle, and the region for the fixed particle is set as the remaining region. Moreover, for the temperature control particle, an operator is requested to designate the boundary between the temperature control particle and the free particle among the region set for both the temperature control particle and the free particle.

FIG. 6 is a flowchart illustrating a processing sequence for setting a fixed particle, according to an embodiment of the present invention. Therefore, FIG. 6 corresponds to the process illustrated in step S230 in FIG. 4.

Here, an operator designates the region combining the regions for the temperature control particle and free particle. Setting unit 10 designates a region, except for the region designated from that of the substrate particle as a whole, as the region for the fixed particle and computes the coordinate value of each particle corresponding to the fixed particle.

More specifically, referring now to FIG. 6, in step S231, an operator is requested to input the range of the X coordinate, the range of the Y coordinate and the lower limit value of the Z coordinate with the slider and numerical value in setting display 730 of FIG. 3, as the coordinates of the vertex points of a rectangular parallelepiped or a parallelepiped (region including the fixed particle and temperature control particle). (In FIG. 3, a rectangular parallelepiped is used, but when the substrate particle is a crystal, the individual coordinate system of crystal is stored in crystal structure DB 52 and when the coordinate system is used, it is converted to the parallelepiped because the coordinate axes are not orthogonally crossing.)

From step S231, the process moves to step S232 where initial motion diagram displaying unit 12 displays the region (region combining the regions for temperature control particle and free particle) for setting the fixed particle as the rectangular parallelepiped or the parallelepiped. Simultaneously, the fixed particle is displayed in a mode (color, etc.) corresponding to the attribute (fixed particle).

From step S232, the process moves to step S233, where, on the basis of contents preset by an operator, the coordinates of each fixed particle is computed and the attribute of the particle corresponding to the relevant coordinate value is set to the fixed particle. This setting content is stored in the kinetic conditions setting file 70 illustrated in FIG. 15, which also stores the setting information of the adsorbate particle.

Referring to FIG. 15, information about the substrate particle is stored in rows 86, 87, 88 in kinetic conditions setting file 70. row 86 indicates the number of atoms forming the substrate particle. In the example in FIG. 15, the number of atoms is set to 500. Row 87 stores the coordinate values of each atom forming the substrate particle. In this example, since the number of atoms is 500, the 500 coordinate values are stored. Row 88 stores the attribute of each atom specified by the coordinate value of row 87, namely the kinetic attribute of each atom. "0" indicates the atom makes free motion (a free atom), "1" indicates the atom does not change temperature due to the influence of the other atom (atom in the constant temperature), and "2" indicates the atom does not move due to the influence of the other atom (fixed atom).

FIG. 7 is a flowchart illustrating a processing sequence for setting a temperature control particle, according to an embodiments of the present invention. In step S221, via setting display 720 in FIG. 3, an operator is requested to designate the region specified by the fixed particle setting process, namely, the boundary between the temperature control particle and free particle. When an operator designates the Z coordinate value of the boundary between the temperature control particle and free particle with the slider or numeral input through the setting display 720 of FIG. 3, the range of the temperature control particle is defined by the Z coordinate value of the lower limit of the region designated by the fixed particle setting process, namely, the region combining the regions for the temperature control particle and the free particle and by the Z coordinate values designated this time. Subsequently, the four coordinates forming the plane at the boundary between the temperature control particle and its upper side is computed from the four vertex points of the bottom plane of the substrate particle as a whole and the Z coordinate value displayed in the display format 750 of FIG. 3.

From step S221, the process moves to step S222 where, based on the four coordinate values computed, the plane at the boundary of the temperature control particle is displayed. Simultaneously, the temperature control particle and the free particle are displayed in the mode (color, etc. for identifying the other attribute) corresponding to respective attributes.

From step S222, the process moves to step S233, where information relating to the temperature control particle is stored in kinetic conditions setting file 70 of FIG. 15. Attribute information of the free particle is also stored in kinetic conditions setting file 70. Namely, in step S223, an operator obtains, regarding the particle in the range which he has designated on the display format, the particle included in the coordinate range which he has designated and then sets the attribute value of the particle corresponding to the kinetic conditions setting file 70 of FIG. 15 to "1" (temperature control).

Moreover, setting display 760 of FIG. 3 designates the viewing direction of the figure of graphic display on display format 750. More specifically, setting display 760 designates, for example, a rotation angle around the X axis, Y axis and Z axis.

FIG. 8 is a diagram illustrating a display format for setting an adsorbate particle generation schedule, according to an embodiment of the present invention. Referring now to FIG. 8, a setting display 800 lists types of adsorbate particles. "n-pentane" is selected in FIG. 8 as a type of adsorbate particle. A region 810 displays the total number of steps of simulation. A region 820 displays the total time (ps) of simulation. These values are set and do not change depending on the type of adsorbate particle. Moreover, a region 830 sets either an equal or a random generation interval for each adsorbate particle. A region 840 designates the number of generation steps, and a region 850 designates the number of particles. This example indicates that five (5) particles are generated during the generation steps 1 to 5000, and that no particles are generated during the generation steps 5001 to 10001. The contents being set here are stored in kinetic conditions setting file 70 of FIG. 15. Rows 71 to 83 of kinetic conditions setting file 70 store data for each type of adsorbate particle. More specifically, the information in region 830, indicating whether the generation interval is equal or random, is stored in the rows 77. The information in region 840, relating to the number of steps, is stored in rows 79. The information in region 850, relating to the number of particles, is stored in rows 80.

FIG. 9 is a diagram illustrating a display format for setting physical conditions of an adsorbate particle, according to an embodiment of the present invention.

Referring now to FIG. 9, a region 760 lists types of adsorbate particles, and regions 770, 780 and 790 set the physical condition when the adsorbate particle selected from region 760 is generated. In region 770, the initial temperature is set. There is the relationship expressed by the following formula and the adsorbate particle generating velocity can be computed from this preset temperature.

$$\tfrac{1}{2}*M*V^2 = \tfrac{3}{2}*Kb*T, \text{ where}$$

M: Mass; V: Velocity; Kb: Boltzmann's constant;
T: Temperature

"All" and "None" in region 790 are items for selectively designating whether velocity should be provided to each atom forming the adsorbate particle. The item "Orientation . . . " is provided for selectively designating the direction of the adsorbate particle when each adsorbate particle is generated. When this item is selected, the format for setting the direction of the adsorbate particle is displayed as in FIG. 10. Moreover, "Direction . . . " selectively designates whether the adsorbate particle generating direction (velocity direction of center of mass of the adsorbate particle) when each adsorbate particle is generated should be designated or not. When this item is selected, the format for setting the adsorbate particle generating direction is displayed as in FIG. 11.

When "All" is set in region 790, then "0" is stored in row 74 of kinetic conditions setting file 70 in FIG. 15. When "None" is set in region 790, the "1" is stored in row 74 of kinetic conditions setting file 70.

Figure 10:
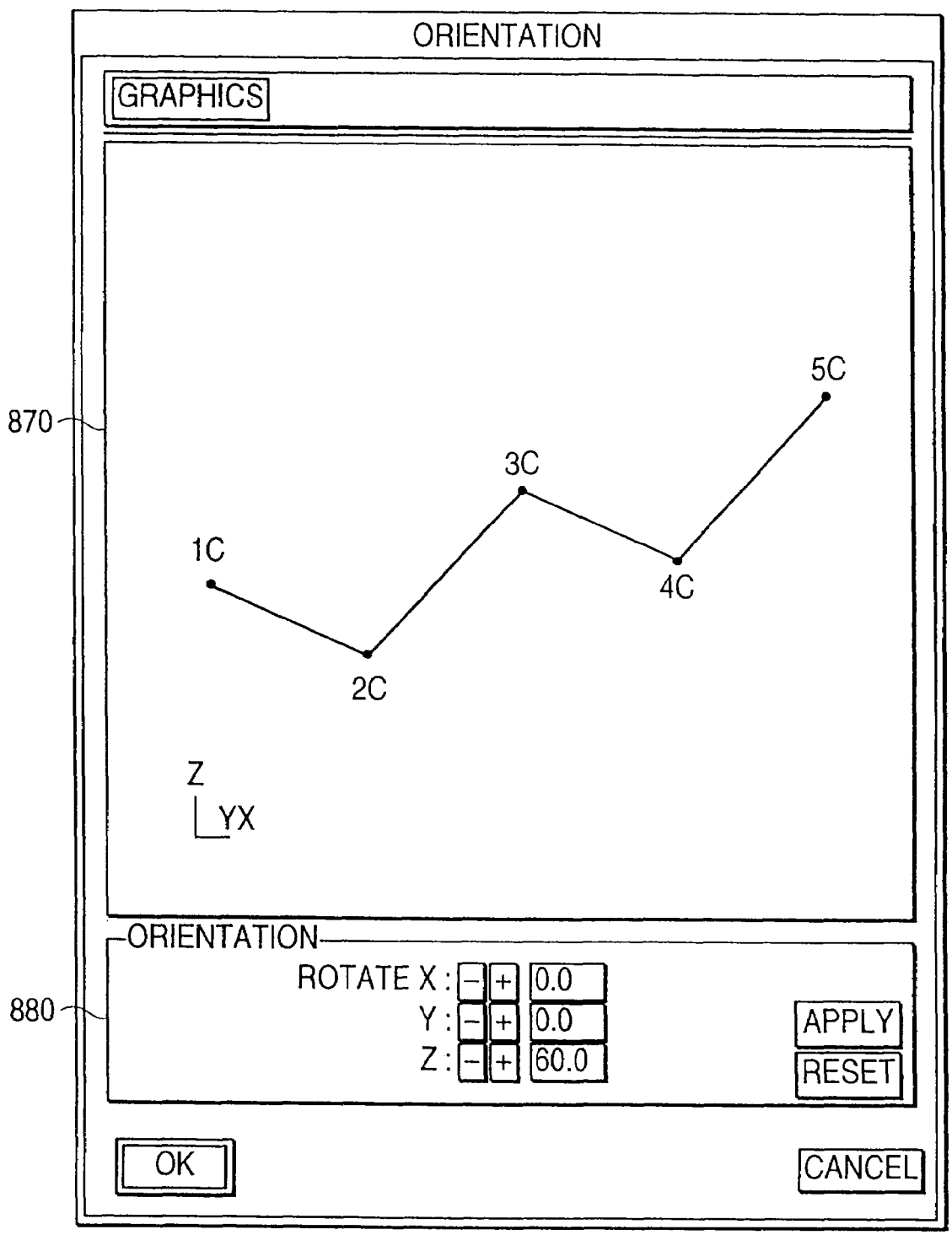
FIG. 10 is a diagram illustrating a display format for setting a direction of an adsorbate particle, according to an embodiment of the present invention.

When "Orientation . . . " is selected in region 790, the adsorbate particle direction (orientation) setting display format of FIG. 10 is displayed, thereby allowing an operator to set the orientation by observing the molecular structure of the adsorbate particle being displayed in display region 870. Setting can be made by designating the rotating angles around the X axis, Y axis and Z axis in setting region 880. The values set here are also stored in kinetic conditions setting file 70 (although not illustrated in FIG. 15). However, when "All" for giving the velocity to the atom is selected in the selecting process for "All" and "None", designation for "Orientation . . . " is impossible. When "Orientation . . . " is not selected, the direction stored in molecule DB 51 is used for the computation.

When "Orientation . . . " is selected, the setting format of FIG. 11 is displayed. This setting format includes the selection item "Fix" for designating only one direction and the selection item "Random" for designating the direction with the range to randomly generate the particle within this range. When "Fix" is designated, it is requested to designate its direction and the result is then displayed as the direction as indicated by display format 752 in region 750 of FIG. 3. (However, the display in region 752 of FIG. 3 appears when "Random" is designated.)

Figure 12:
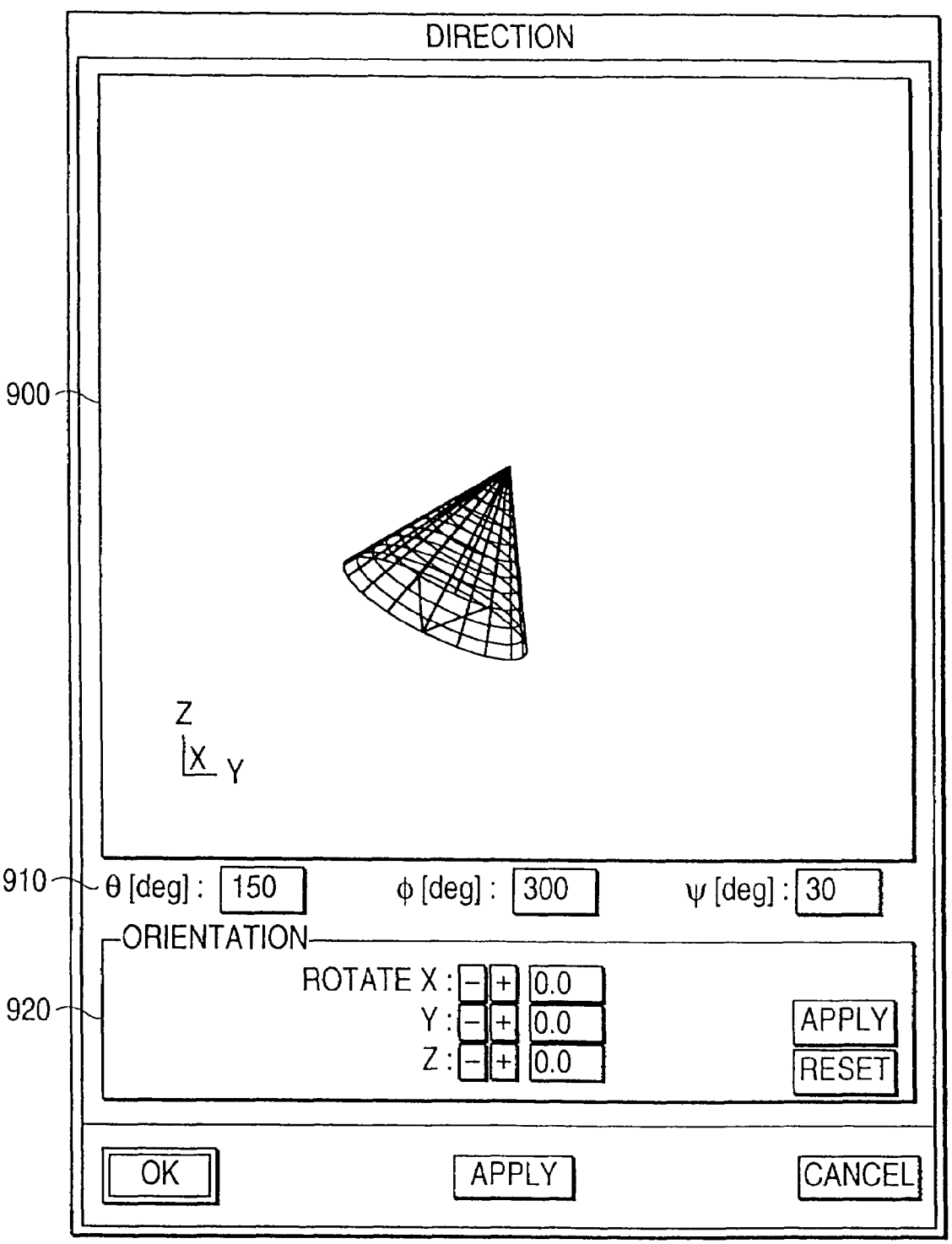
FIG. 12 is a diagram illustrating a display format for setting an adsorbate particle ejecting direction, according to an embodiment of the present invention.

When "Random" is designated, the setting format of FIG. 12 is displayed. This display shows that the adsorbate particle is generated within the range of dispersion of a cone displayed in a display region 900 of FIG. 12. In the setting format of FIG. 12, shape (expansion) and direction of cone are designated. Expansion is set by ψ. In regard to the direction, inclination of the axis of the cone is set by an angle θ formed against the Z axis and by an angle φ formed against the X axis. On the basis of this setting content, display region 900 of FIG. 12 is displayed. At the lower part of the display in display region 900, the substrate particle exists. Moreover, when the setting format of FIG. 3 is displayed after this setting, the diagram in display region 752 is displayed on the basis of the direction ψ (expansion) providing the possibility for generation of adsorbate particle preset in FIG. 12.

The preset θ, φ, ψ are stored in rows 81, 82, 83, respectively, of kinetic conditions setting file 70.

Figure 13:
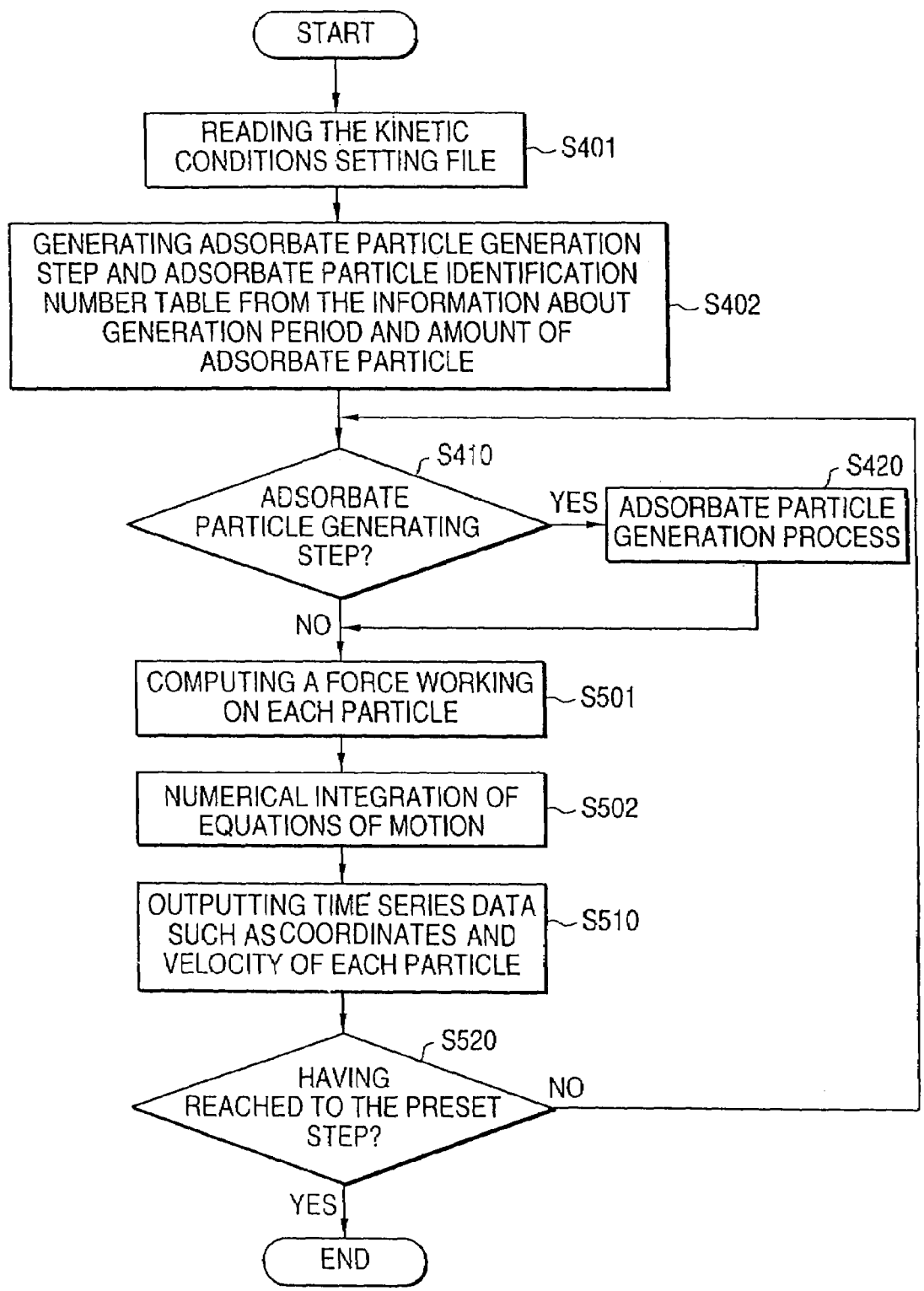
FIG. 13 is a flowchart illustrating a processing sequence for computing molecule motion, according to an embodiment of the present invention.

FIG. 13 is a flowchart illustrating a processing sequence for computing molecule motion, according to an embodiment of the present invention. More specifically, FIG. 13 is a more detailed illustration of various steps following step S400 in FIG. 2. Therefore, some steps in FIG. 13 are provided with the same step number as in FIG. 2.

Referring now to FIG. 13, in step S401, kinetic conditions setting file 70 is read, since this file is necessary for computation of molecule motion. From step S401, the process moves to step S402 where a table storing the adsorbate particle generation step and adsorbate particle identification number is generated from the information relating to generation period and amount of adsorbate particle stored in kinetic conditions setting file 70. A format of the table to be generated is shown in FIG. 16.

For example, in FIG. 15, row 72 of kinetic conditions setting file 70 stores the identification numbers of adsorbate particles. The identifier "3" is stored at the extreme right side of column 72, indicating that information about the adsorbate particle having the identifier "3" is stored at the extreme left side of all columns. Information about the generation period of an adsorbate particle is stored in row 79 and the amount of adsorbate particle generated is stored in row 80. The data stored in these columns suggests that one adsorbate particle is generated during the generation steps 1 to 1000, two adsorbate particles are generated during the generation steps 1000 to 2000 and no adsorbate particles are generated after the generation step 2000. Moreover, information about how the adsorbate particles are generated is stored in row 77. Therefore, row 77 indicates that the adsorbate particle having the identifier "3" is generated in unequal intervals.

When an adsorbate particle is generated in equal intervals, the generation interval of one adsorbate particle can be determined by dividing the generation step interval by the number of adsorbate particles generation during the generation step interval. For example, as indicated by row 77 of kinetic conditions setting file 70, adsorbate particle having the identifier "3" is generated in equal intervals. However, for explanation purposes, assume that the adsorbate particle having the identifier "3" is generated at equal intervals. In this case, as indicated by row 79, there are 1000 generation steps between the generation step 1000 and the generation step 2000. In addition, as indicated by row 80, two (2) adsorbate particles having the identifier "3" are to be generation during this time. Therefore, the generation step interval would equal five-hundred (500), which is the generation step interval (1000) divided by the number of adsorbate particles generation (2).

When the adsorbate particle is generated in unequal intervals, the step for generating the adsorbate particle is obtained by generating a random number and adding a remainder obtained by dividing the random number with the number of generation steps between the starting generation step of each generation period. For example, there are one-thousand (1000) steps between the starting generation steps 1000 and 2000. This computation is performed to determine a generation step for generating each adsorbate particle. The table in FIG. 16 stores the above-computed generation time (step number) for each adsorbate particle. For example, the table in FIG. 16 shows that the adsorbate particle having the identifier "3" is generated in the steps 1222 and 1606.

Referring again to FIG. 13, from step S402, the process moves to step S410. The steps after step S410 are executed after the actual simulation time (count for the number of generation steps) is started. First, in step S410, it is determined whether the current time is an adsorbate particle generation step by referring to the adsorbate particle generation table of FIG. 16. When the process is not at an adsorbate particle generation step in step S410, the process moves to step S501. When the process is at an adsorbate particle generation step in step S410, the process moves to step S420 where the corresponding adsorbate particle is generated. From step S420, the process moves to step S501.

In step S501, forces working between the generated adsorbate particles and earlier generated substrate particles are computed. From step S501, the process moves to step S502 where, from the forces working between the adsorbate particles and the substrate particles, the current coordinates of each particle and velocity are computed using the numerical integration of equations of motion. From step S502, the process moves to step S510, where the result obtained is stored in time series memory unit 4 as time series data (that is, data arranged on a time series basis).

From step S510, the process moves to step S520 where it is determined whether the process has reached the final generation step. If the process is not at the final generation step, the process returns to step S410 to determine whether additional adsorbate particles are to be generated. If the process is at the final generation step in step, S520, the process ends.

FIG. 14 is a flowchart illustrating a processing sequence for generating an adsorbate particle, according to an embodiment of the present invention. Therefore, FIG. 14 illustrates the details of step S420 in FIG. 13.

In step S421, an adsorbate particle emission source position is computed using random numbers. The positions where the adsorbate particles are generated are defined as the regions in rows 84, 85 of kinetic conditions setting file 70. Positions can be computed by obtaining the coordinate values in the region where the random numbers are generated twice. That is, a random number is generated and the remainder obtained by dividing such random number with the length of region in the X direction is defined as the position in the X direction. Thereafter, a random number is generated again and the remainder obtained by dividing the random number with the length of region in the Y direction is defined as the position in the Y direction.

From step S421, the process moves to step S422 where it is determined whether the atom forming the adsorbate particle should be static against the center of mass of particle. First, with reference to the adsorbate particle generation table, the identifier of the adsorbate particle to be generated is obtained and reference should be made to row 74 of kinetic conditions setting file 70 using the identifier of this adsorbate particle. When "1" is stored in row 74, it is not required to give the velocity to each atom. Therefore, from step S422, the process moves to step S425. However, when "0" is stored in row 74, each atom is to be provided with a velocity. In this case, from step S422, the process moves to step S423.

In step S423, the orientation of the adsorbate particle is determined. In this case, random numbers are generated in the orientations of particle ($\theta$, $\phi$, $\psi$) to obtain random orientations. From step S423, the process moves to step S424 where an initial velocity is given to the atoms forming the particle. For this purpose, the tentative initial velocity of each atom is computed on the basis of the following conditions, considering the condition that the center of mass of the adsorbate particle as a whole is fixed.

Total sum of momentum of atoms is zero ($\Sigma Mi*Vi=0$)

Interrelation equation of temperature and velocity $$(\Sigma \tfrac{1}{2}*Mi*Vi^2=(3N-3)/2*Kb*T), where$$

Mi: Mass of atom; Vi: Velocity of atom;

N: Number of atoms forming the particle;

Kb: Boltzmann's constant;

T: Initial temperature of particle; and (3N−3) indicates that a degree of freedom "3" of the translation of particle is subtracted.

First, from the relationship of temperature and velocity, the x, y, z components of the initial velocity of each atom among N/2 atoms of N atoms in total are computed from the following equations by uniformly generating random numbers in the predetermined ranges of $\theta$, $\phi$ ($0<=\theta<=2\pi$, $0<=\phi<=\pi$). (Where, if the number of atoms N is not an even number, computation should be executed for $(N-1)/2$ and the velocity of one atom should, for example, be zero.)

$$Vix = ((3N-3)/\sum(1/Mi)*Kb*T)^{(1/2)} *$$
$$1/Mi*\sin\theta*\cos\phi$$
$$= \alpha*\sin\theta*\cos\theta$$
$$Viy = \alpha*1/Mi*\sin\theta*\cos\phi$$
$$Viz = \alpha*1/Mi*\cos\phi$$

Next, since the total sum of the momentum of the atoms is zero, velocity of one atom which makes zero the sum with momentum of one atom obtained previously is computed from the following equation (this computation should be performed for the number of times as many as N/2).

$$Vjx = -Mi/Mj*Vix$$
$$Vjy = -Mi/Mj*Viy$$
$$Vjz = -Mi/Mj*Viz$$

In the step S425, a random number is obtained to set the direction of the center of mass velocity of the adsorbate particle so that the angle formed between this direction and the Z axis is ranged from 0 to ψ degrees. From step S425, the process moves to step S426 where the direction of center of mass velocity of the adsorbate particle obtained here is rotated by φ degrees around the Z axis. From step S426, the process moves to step S427 where the direction of center of mass velocity of the adsorbate particle is further rotated by θ degrees around the X' axis of the coordinate system O-X'Y'X' obtained in above rotating process. From step S427, the process moves to step S428 where, on the basis of the velocity direction, the center of mass velocity of the adsorbate particle is added to the tentative initial velocity of each atom forming the adsorbate particle.

As explained above, the center of mass velocity can be computed from the following equation and the temperature information stored in kinetic conditions setting file 70.

$$\tfrac{1}{2}*M*V^2 = \tfrac{3}{2}*Kb*T, \text{ where}$$

M: Mass; V: Velocity; Kb: Boltzmann's constant; and T: Temperature

If an adsorbate particle was selected from molecular structure DB 51, crystal structure DB 52 or molecular crystal DB 52, then the mass M should be obtained from information stored in the appropriate database.

According to the above embodiments of the present invention, an apparatus simulates phenomena of a combined particle formed of substrate particles and adsorbate particles. Here, a combined particle refers, for example, to a particle formed of a combination of individual atoms and/or molecules. Thus, a combined particle is a particle formed of other, smaller particles. The apparatus includes a kinetic condition setting unit and a particle motion computing unit. The kinetic condition setting unit sets information for defining initial, kinetic conditions of the adsorbate particles. The particle motion computing unit generates the adsorbate particles in accordance with the information set by the kinetic condition setting unit and computes motion of the generated adsorbate particles, to simulate phenomena of the combined particle. For example, the information set by the kinetic condition setting unit can define a plurality of generation periods and a corresponding number of adsorbate particles to be generated during each generation period by the particle motion computing unit.

In addition, according to the above embodiments of the present invention, the information set by the kinetic condition setting unit can include information for defining kinetic conditions of the substrate particles. In this case, the particle motion computing unit can generate the substrate particles before generating the adsorbate particles.

Further, according to the above embodiments of the present invention, each substrate particle typically includes a fixed particle, a temperature control particle and a free particle. The information set by the kinetic condition setting unit can include information for defining kinetic conditions of the fixed particle, the temperature control particle and the free particle of each substrate particle. In this case, the particle motion computing unit generates the fixed particle, the temperature control particle and the free particle of each substrate particle in accordance with the information set by the kinetic condition setting unit.

Further, according to the above embodiments of the present invention, each adsorbate particle includes a plurality of smaller particles, such as atoms or molecules. The information set by the kinetic condition setting unit includes information indicating whether the smaller particles of a respective adsorbate particle are static against a center of mass of the adsorbate particle. When the particle motion computing unit generates an adsorbate particle and the information set by the kinetic condition setting unit indicates that the smaller particles of the respective adsorbate particle are not static against the center of mass, the particle motion computing unit provides a random orientation to the smaller particles of the adsorbate particle. See, for example, steps S422 and S423 in FIG. 14. Further, in this case, the particle motion computing unit provides an initial velocity to the smaller particles of the adsorbate particle. See, for example, step S424 in FIG. 14. In addition, according to above embodiments of the present invention, when generating an adsorbate particle, the particle motion computing unit can provide a random direction of center of mass velocity of the adsorbate particle. See, for example, step S425 in FIG. 14.

Therefore, the above embodiments of the present invention provide a flexible simulation system to process various phenomena such as adsorption, crystal growth and surface damage. Moreover, the flexible simulation system according to the above embodiments of the present invention can consider a plurality of atoms, molecules and particles to encompass initial conditions of many simulations and can realize unified operability. In addition, the flexible simulation system according to the above embodiments of the present invention considers the motion itself, or the timing of the motion, of a particle and the initial position of the particle.

Accordingly, the above embodiments of the present invention allow, with similar manipulation, various different processes to deal with a variety of phenomena such as adsorption, crystal growth and surface damage. Moreover, an operator can easily understand a degree of changes (that is, a degree of influence) of parameter values to be set or changed.

The above embodiments of the present invention relate to the simulation of various "particles". A "particle" can refer to many different objects. For example, a "particle" can be an atom, a molecule, or a material composed of molecules and/or atoms.

The present invention relates to simulating particles formed of substrate particles and adsorbate particles. However, the embodiments of the present invention are not intended to be limited to particles formed of substrate particles and adsorbate particles.

Although a few preferred embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An apparatus for simulating phenomena of a particle formed of adsorbate particles and substrate particles, comprising:
a kinetic condition setting unit which sets information for defining a plurality of generation periods and a corresponding number of adsorbate particles to be generated during each generation period wherein the information can include a position of a corresponding emission source, a temperature, a chemical composition of the particle, a region, a physical condition, a velocity of each atom forming the particle, and a direction; and
a particle motion computing unit which generates the adsorbate particles in accordance with the information set by the kinetic condition setting unit and computes motion of the generated adsorbate particles, to simulate phenomena of said particle formed of adsorbate particles and substrate particles, each adsorbate particle having a corresponding emission source wherein
for each adsorbate particle, the kinetic condition setting unit sets a region indicating a position of the corresponding emission source, and
the particle motion computing unit generates each adsorbate particle in accordance with the position of the corresponding emission source.

2. An apparatus as in claim 1, wherein
before generating the adsorbate particles, the particle motion computing unit generates the substrate particles.

3. An apparatus as in claim 1, further comprising:
a display which allows a user to enter the information set by the kinetic condition setting unit.

4. An apparatus as in claim 1, wherein
the kinetic condition setting unit sets information for generating the substrate particles.

5. An apparatus as in claim 1, wherein
each adsorbate particle is formed of atoms;
the information set by the kinetic condition setting unit includes information indicating whether the atoms of a respective adsorbate particle are static against a center of mass of the adsorbate particle; and
when the particle motion computing unit generates an adsorbate particle and the information set by the kinetic condition setting unit indicates that the atoms of the respective adsorbate particle are not static against the center of mass, the particle motion computing unit provides a random orientation to the atoms of the adsorbate particle.

6. An apparatus as in claim 5, further comprising:
a display which allows a user to enter the information set by the kinetic condition setting unit.

7. An apparatus as in claim 1, wherein
each adsorbate particle is formed of atoms;
the information set by the kinetic condition setting unit includes information indicating whether the atoms of a respective adsorbate particle are static against a center of mass of the adsorbate particle; and
when the particle motion computing unit generates an adsorbate particle and the information set by the kinetic condition setting unit indicates that the atoms of the respective adsorbate particle are not static against the center of mass, the particle motion computing unit provides an initial velocity to the atoms of the adsorbate particle.

8. An apparatus as in claim 1, wherein, when generating an adsorbate particle, the particle motion computing unit provides a random direction within a cone pointed at a substrate and being centered at a point of generation of center of mass velocity of the adsorbate particle.

9. An apparatus as in claim 1, further comprising:
a display which displays the information set by the kinetic condition setting unit.

10. An apparatus for simulating phenomena of a particle formed of adsorbate particles and substrate particles, each adsorbate particle having a corresponding emission source, the apparatus comprising:
an input device which allows a user to designate a region;
a kinetic condition setting unit which, for each adsorbate particle, sets the region designed by the user as a region indicating a position of the corresponding emission source; and
a particle motion computing unit which generates the adsorbate particles in accordance with the position of the corresponding emission source as indicated by the region designated by the user and computes motion of the generated adsorbate particles, to simulate phenomena of said particle formed of adsorbate particles and substrate particles.

11. An apparatus as in claim 10, wherein the input device is a display.

12. An apparatus as in claim 10, further comprising:
a display which displays the information set by the kinetic condition setting unit.

13. An apparatus as in claim 12, wherein the display shows the adsorbate particles generated by the particle motion computing unit and indicates the motion computed by the particle motion computing unit.

14. An apparatus for simulating phenomena of a particle formed of adsorbate particles and substrate particles, each adsorbate particle having a corresponding emission source, the apparatus comprising:
a kinetic condition setting unit which sets information for defining kinetic conditions of the adsorbate particles wherein the information can include a position of a corresponding emission source, a temperature, a chemical composition of the particle, a region, a physical condition, a velocity of each atom forming the particle, and a direction; and
a particle motion computing unit which generates the adsorbate particles in accordance with the information set by the kinetic condition setting unit and the position of the corresponding emission source, and computes motion of the generated adsorbate particles, to simulate phenomena of said particle formed of adsorbate particles and substrate particles, each adsorbate particle having a corresponding emission source.

15. An apparatus as in claim 14, wherein
the adsorbate particles move towards the substrate particles,
the kinetic condition setting unit sets a region for defining an initial position of the adsorbate particles, and
the apparatus further comprises a display which displays the relationship between the region set by the kinetic condition setting unit and a region indicating a position of a substrate particle forming said particle formed of adsorbate particles and substrate particles.

16. An apparatus as in claim 15, wherein
the kinetic condition setting unit sets information for providing a direction of velocity to the adsorbate particles, and
the display shows the direction of velocity with respect to the region set by the kinetic condition setting unit and the region indicating the position of a respective substrate particle.

17. An apparatus as in claim 14, further comprising:
a display which displays the information set by the kinetic condition setting unit.

18. A computer-implemented method for simulating phenomena of a particle formed of adsorbate particles and substrate particles, each adsorbate particle having a corresponding emission source, the method comprising the steps of:
setting information for defining a plurality of generation periods and a corresponding number of adsorbate particles to be generated during each generation period wherein the information can include a position of a corresponding emission source, a temperature, a chemical composition of the particle, a region, a physical condition, a velocity of each atom forming the particle, and a direction;
generating the adsorbate particles in accordance with the information set in the setting step and the position of the corresponding emission sources;
computing motion of the generated adsorbate particles; and
simulating phenomena of said particle formed of adsorbate particles and substrate particles in accordance with the computed motion.

19. A computer-implemented method for simulating phenomena of a particle formed of adsorbate particles and substrate particles, each adsorbate particle having a corresponding emission source, the method comprising the steps of:
setting, for each adsorbate particle, a region indicating a position of the corresponding emission source;
generating the adsorbate particles in accordance with the position of the corresponding emission source as indicated by the region set in the setting step;
computing motion of the generated adsorbate particles; and
simulating phenomena of said particle formed of adsorbate particles and substrate particles in accordance with the computed motion.

20. A method for simulating phenomena of a particle formed of adsorbate particles and substrate particles, each adsorbate particle having a corresponding emission source, the method comprising:
setting information for defining kinetic conditions of the adsorbate particles wherein the information can include a position of a corresponding emission source, a temperature, a chemical composition of the particle, a region, a physical condition, a velocity of each atom forming the particle, and a direction;
displaying the set information;
generating the adsorbate particles in accordance with the set information and the positions of the corresponding emission sources; and
computing motion of the generated adsorbate particles, to simulate phenomena of said particle formed of adsorbate particles and substrate particles, each adsorbate particle having a corresponding emission source.

21. An apparatus for simulating phenomena of a particle formed with adsorbate particles, comprising:
a kinetic condition setting unit which sets information for defining kinetic conditions of the adsorbate particles wherein the information can include a position of a corresponding emission source, a temperature, a chemical composition of the particle, a region, a physical condition, a velocity of each atom forming the particle, and a direction; and
a particle motion computing unit which generates the adsorbate particles in accordance with the information set by the kinetic condition setting unit and computes motion of the generated adsorbate particles, to simulate phenomena of said particle formed with adsorbate particles, each adsorbate particle having a corresponding emission source, wherein
for each adsorbate particle, the kinetic condition setting unit sets a region indicating a position of the corresponding emission source, and
the particle motion computing unit generates each adsorbate particle in accordance with the position of the corresponding emission source as indicated by the region set by the kinetic condition setting unit.

22. An apparatus as in claim 21, wherein the information set by the kinetic condition setting unit defines a plurality of generation periods and a corresponding number of adsorbate particles to be generated during each generation period by the particle motion computing unit.

23. An apparatus as in claim 21, wherein
said particle formed with adsorbate particles is formed with both adsorbate particles and substrate particles,
the information set by the kinetic condition setting unit includes information for defining kinetic conditions of the substrate particles, and
the particle motion computing unit generates the substrate particles before generating the adsorbate particles.

24. An apparatus as in claim 21, wherein p1 said particle formed with adsorbate particles is formed with both adsorbate particles and substrate particles,
each substrate particle includes a fixed particle and a temperature control particle,
the information set by the kinetic condition setting unit includes information for defining kinetic conditions of the fixed particle and the temperature control particle, and
the particle motion computing unit generates the fixed particle and the temperature control particle of each substrate particle in accordance with the information set by the kinetic condition setting unit.

25. An apparatus as in claim 21, further comprising:
a display which displays the information set by the kinetic condition setting unit.

26. An apparatus as in claim 21, wherein
each adsorbate particle includes a plurality of atoms;
the information set by the kinetic condition setting unit includes information indicating whether the atoms of a respective adsorbate particle are static against a center of mass of the adsorbate particle; and
when the particle motion computing unit generates an adsorbate particle and the information set by the kinetic condition setting unit indicates that the atoms of the respective adsorbate particle are not static against the center of mass, the particle motion computing unit provides a random orientation to the atoms of the adsorbate particle.

27. An apparatus as in claim 26, wherein, when the particle motion computing unit generates an adsorbate particle and the information set by the kinetic condition setting unit indicates that the atoms of the respective adsorbate particle are not fixed against center of mass, the particle motion computing unit provides an initial velocity to the atoms of the adsorbate particle.

28. An apparatus as in claim 21, wherein, when generating an adsorbate particle, the particle motion computing unit provides a random direction within a cone pointed at a substrate and being centered at a point of generation of center of mass velocity of the adsorbate particle.

* * * * *

UNITED STATES PATENT AND TRADEMARK OFFICE
CERTIFICATE OF CORRECTION

| | |
|---|---|
| PATENT NO. | : 7,231,332 B2 |
| APPLICATION NO. | : 08/889440 |
| DATED | : June 12, 2007 |
| INVENTOR(S) | : Munetaka Takeuchi et al. |

It is certified that error appears in the above-identified patent and that said Letters Patent is hereby corrected as shown below:

On the title page item (56), Column 2 (Other Publications), Line 6, change "Electron-Imapct" to --Electron-Impact--.

Column 18, Line 35, after "wherein" delete "p1".

Signed and Sealed this

Twentieth Day of November, 2007

JON W. DUDAS
*Director of the United States Patent and Trademark Office*